United States Patent
Gerber et al.

(10) Patent No.: US 8,554,339 B2
(45) Date of Patent: Oct. 8, 2013

(54) ANCHOR ASSEMBLY FOR USE IN OCCIPITAL NERVE STIMULATION

(75) Inventors: Martin T. Gerber, Maple Grove, MN (US); Michael D. Baudino, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 141 days.

(21) Appl. No.: 13/010,872

(22) Filed: Jan. 21, 2011

(65) Prior Publication Data

US 2011/0190857 A1  Aug. 4, 2011

Related U.S. Application Data

(60) Provisional application No. 61/299,647, filed on Jan. 29, 2010.

(51) Int. Cl.
*A61N 1/00* (2006.01)

(52) U.S. Cl.
USPC .......................................... 607/116; 607/117

(58) Field of Classification Search
USPC .................. 607/116–117, 136–137, 139, 149
See application file for complete search history.

(56) References Cited

U.S. PATENT DOCUMENTS

| | | | |
|---|---|---|---|
| 4,519,403 A | 5/1985 | Dickhudt | |
| 4,735,205 A | 4/1988 | Chachques et al. | |
| 5,391,200 A | 2/1995 | KenKnight et al. | |
| 6,205,361 B1 | 3/2001 | Kuzma et al. | |
| 6,482,182 B1 * | 11/2002 | Carroll et al. | 604/174 |
| 6,522,932 B1 | 2/2003 | Kuzma et al. | |
| 6,606,521 B2 | 8/2003 | Paspa et al. | |
| 7,099,718 B1 | 8/2006 | Thacker et al. | |
| 7,177,702 B2 | 2/2007 | Wallace et al. | |
| 7,191,018 B2 | 3/2007 | Gielen et al. | |
| 7,212,867 B2 | 5/2007 | Van Venrooij | |
| 7,376,468 B2 | 5/2008 | King et al. | |
| 7,684,873 B2 | 3/2010 | Gerber | |
| 7,797,054 B2 | 9/2010 | Skubitz et al. | |
| 7,856,277 B1 | 12/2010 | Thacker et al. | |
| 2005/0033395 A1 * | 2/2005 | Seifert et al. | 607/126 |
| 2005/0182390 A1 | 8/2005 | Shanley | |

(Continued)

FOREIGN PATENT DOCUMENTS

| | | |
|---|---|---|
| WO | WO98-17345 | 4/1998 |
| WO | WO2008-048471 | 4/2008 |

OTHER PUBLICATIONS

U.S. Statutory Invention Registration H1905, Oct. 3, 2000 (Hall).

*Primary Examiner* — Christopher D Koharski
*Assistant Examiner* — Catherine Voorhees
(74) *Attorney, Agent, or Firm* — Mueting Raasch & Gebhardt PA

(57) ABSTRACT

A system that includes an anchor assembly, the anchor assembly including: at least one anchoring structure configured to be anchored in a head of a patient; and at least one lead anchoring structure; and b. at least one lead, the at least one lead including a lead body extending from a distal end to a proximal end; at least one electrode located on or in the distal end of the lead body; and at least one lead anchor located on or in the lead body proximal to the electrode, wherein the at least one lead anchor of the lead and the lead anchoring structure are configured to cooperate to secure the at least one lead to the anchor assembly.

8 Claims, 10 Drawing Sheets

(56) References Cited

U.S. PATENT DOCUMENTS

| | | |
|---|---|---|
| 2006/0235502 A1 | 10/2006 | Belluche |
| 2007/0050004 A1 | 3/2007 | Swoyer et al. |
| 2007/0162101 A1 | 7/2007 | Burgermeister et al. |
| 2008/0103572 A1* | 5/2008 | Gerber .................... 607/116 |
| 2008/0103575 A1 | 5/2008 | Gerber |
| 2008/0132969 A1 | 6/2008 | Bennett et al. |
| 2009/0043372 A1 | 2/2009 | Northrop et al. |
| 2009/0088826 A1* | 4/2009 | Bedenbaugh ............... 607/116 |
| 2009/0118807 A1* | 5/2009 | Kowalczyk ............... 607/117 |
| 2009/0198252 A1 | 8/2009 | Seifert et al. |
| 2009/0270957 A1 | 10/2009 | Pianca et al. |
| 2010/0069882 A1 | 3/2010 | Jennings |
| 2010/0082086 A1 | 4/2010 | Zhu |
| 2011/0022142 A1* | 1/2011 | Barker et al. ............... 607/117 |

* cited by examiner

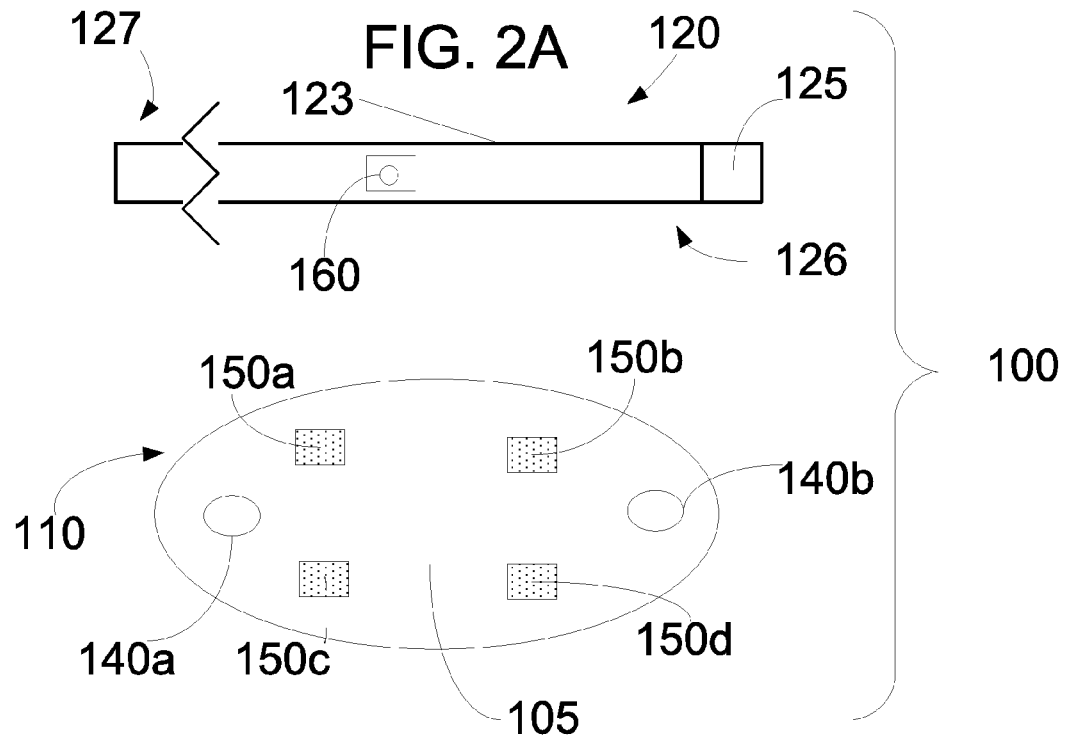
FIG. 2A
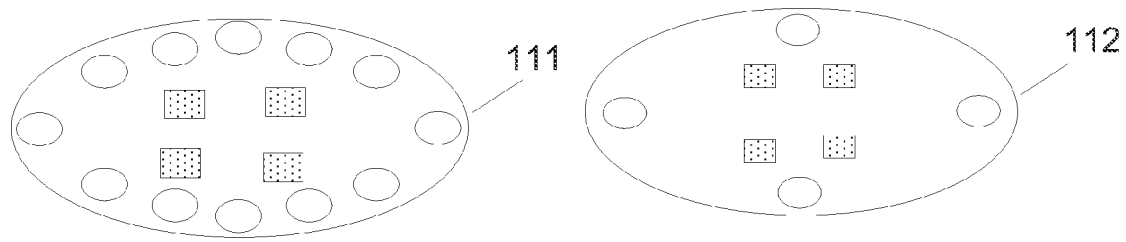
FIG. 2B
FIG. 2C
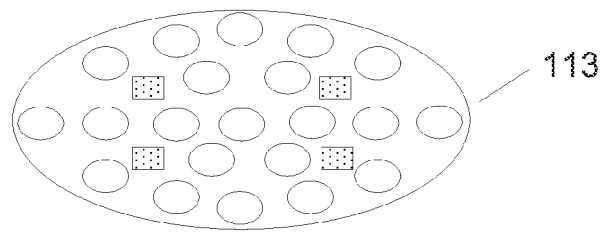
FIG. 2D

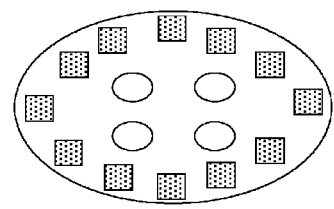
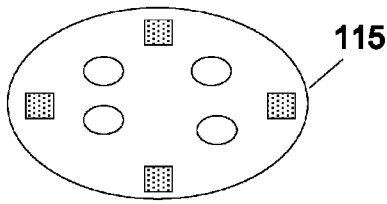
FIG. 2E      FIG. 2F
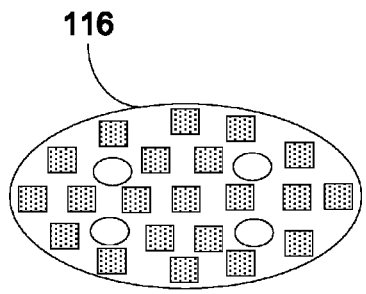
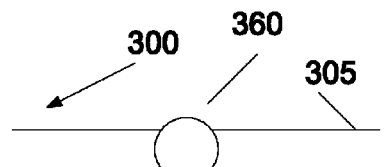
FIG. 2G      FIG. 3A
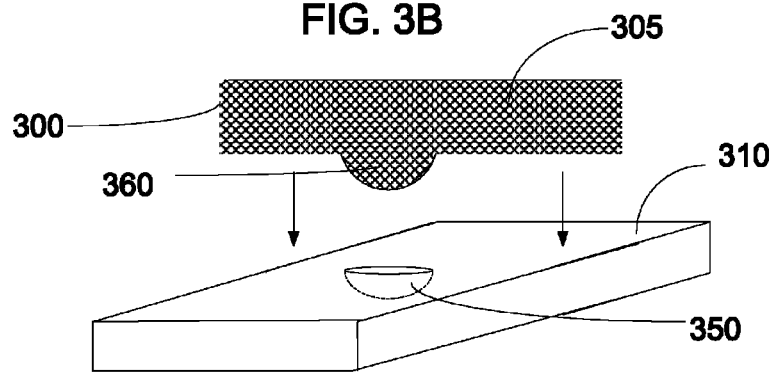
FIG. 3B

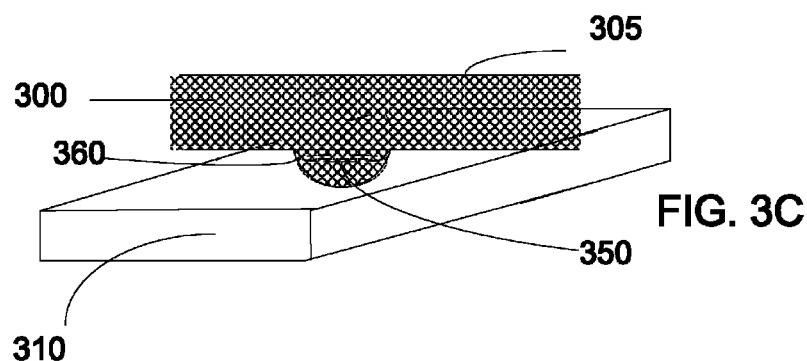
FIG. 3C
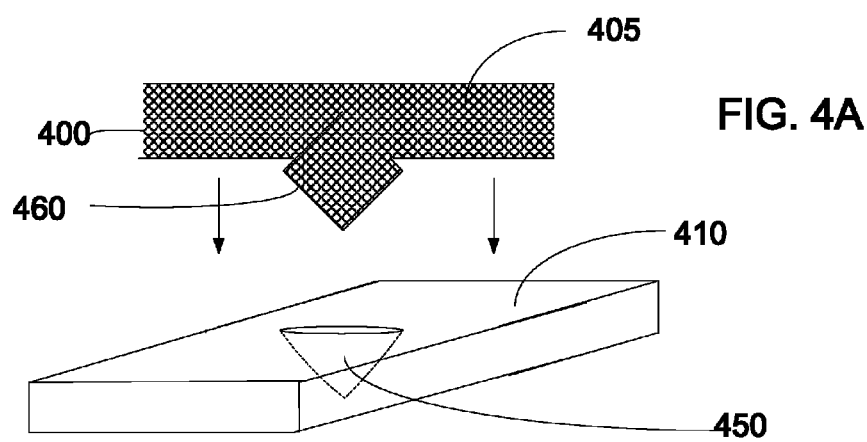
FIG. 4A
FIG. 4B
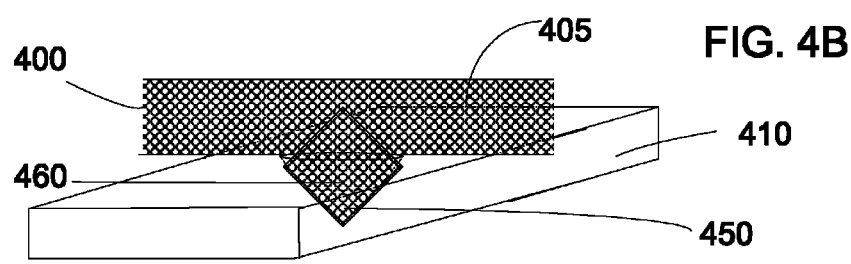

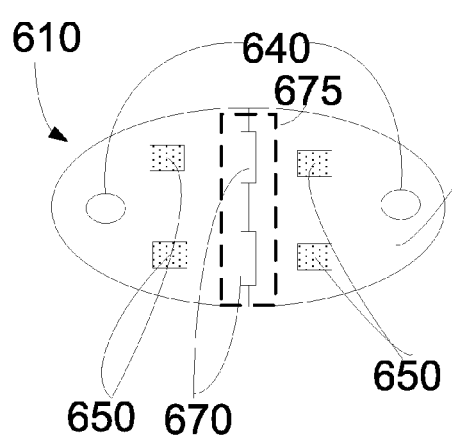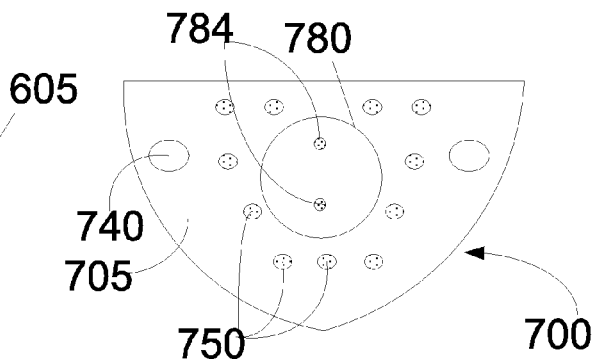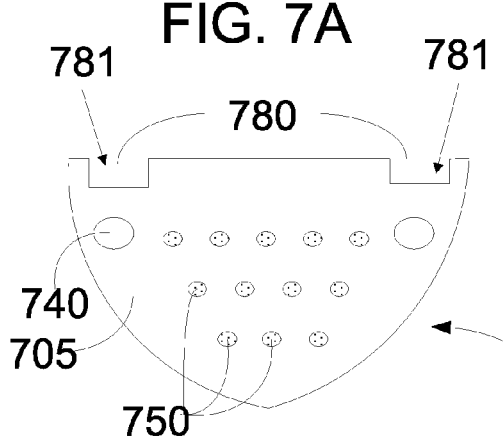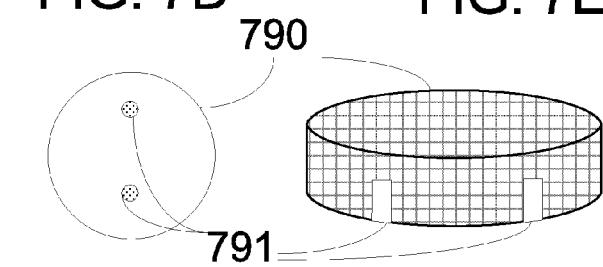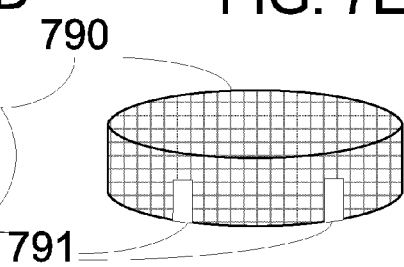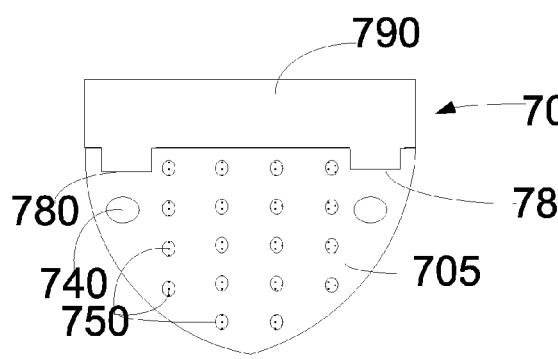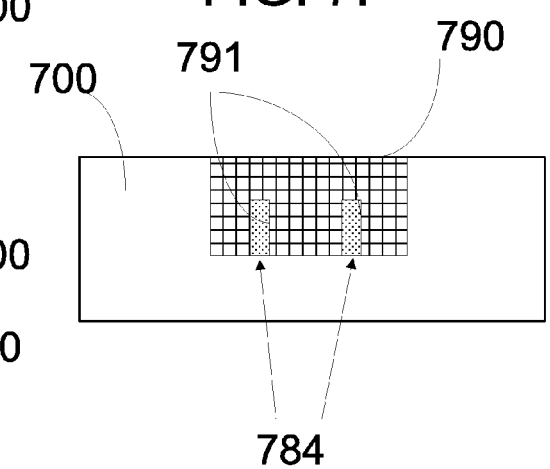

ANCHOR ASSEMBLY FOR USE IN OCCIPITAL NERVE STIMULATION

RELATED APPLICATION

This patent application claims priority to U.S. Provisional Patent Application Ser. No. 61/299,647, filed Jan. 29, 2010, the entire disclosure of which is expressly incorporated herein by reference.

FIELD

The present disclosure relates to implantable medical devices; more particularly to an anchor assembly for occipital nerve stimulation.

BACKGROUND

Headaches, such as migraines, and occipital neuralgia are often incapacitating and may lead to significant consumption of drugs to treat the symptoms. However, a rather large number of people are unresponsive to drug treatment, leaving them to wait out the episode or to resort to coping mechanisms. For refractive occipital neuralgia, nerve ablation or separation may effectively treat the pain.

Occipital nerve stimulation may serve as an alternative for treatment of migraines or occipital neuralgia. For example, a dual channel implantable electrical generator may be implanted subcutaneously in a patient. A distal portion of first and second leads may be implanted in proximity to a left and right occipital nerve such that one or more electrode of the leads are in electrical communication with the occipital nerves. The proximal portions of the leads may then be connected to the signal generator such that electrical signals can be delivered from the signal generator to the electrodes to apply therapeutic signals to the occipital nerves Alternatively, two single channel implantable electrical generators may be employed, where the first lead is connected to one signal generator and the second lead is connected to the second signal generator.

Such methods of treatment generally require a rather extensive surgical procedure to place the stimulator, leads and other components that may be necessary. Decreasing the time necessary for the procedure may make the procedure better tolerated by patients, more adopted by surgeons, or both. Decreasing the amount of components that need to be secured via methods such as suturing could serve to decrease the time necessary to carry out the procedure.

BRIEF SUMMARY

Disclosed herein is an anchor assembly that includes at least one anchoring structure configured to be anchored in a head of a patient; at least one lead anchoring structure; and at least one device anchoring structure.

Disclosed herein is a system that includes an anchor assembly, the anchor assembly including: at least one anchoring structure configured to be anchored in a head of a patient; and at least one lead anchoring structure; and at least one lead, the at least one lead including a lead body extending from a distal end to a proximal end; at least one electrode located on or in the distal end of the lead body; and at least one lead anchor located on or in the lead body proximal to the electrode, wherein the at least one lead anchor of the lead and the lead anchoring structure are configured to cooperate to secure the at least one lead to the anchor assembly.

Also disclosed is a method of anchoring at least one lead in a head of a patient, the method including the steps of anchoring an anchor assembly in the head of the patient, the anchor assembly including at least one anchoring structure configured to be anchored in a head of a patient; and at least one lead anchoring structure; and securing at least one lead to the anchor assembly, the at least one lead including a lead body extending from a distal end to a proximal end; at least one electrode located on or in the distal end of the lead body; and at least one lead anchor located on or in the lead body proximal to the electrode; wherein the at least one lead anchor of the lead and the lead anchoring structure are configured to cooperate to secure the at least one lead to the anchor assembly; thereby anchoring the at least one lead in the head of the patient.

BRIEF DESCRIPTION OF THE DRAWINGS

FIG. 2A is a schematic view of an embodiment of a system disclosed herein that includes a lead and an anchor assembly.

FIGS. 2B, 2C, 2D, 2E, 2F, and 2G are schematic views of exemplary embodiments of anchor assemblies.

FIG. 3A is a schematic view of a portion of a disclosed lead that includes a lead anchor having a spherical configuration.

FIG. 3B is a schematic perspective view of the lead of FIG. 3A with respect to an anchor assembly; and FIG. 3C depicts the lead in cooperation with the lead anchoring structure of the anchor assembly.

FIG. 4A is a schematic perspective view of a lead having a pyramidal configuration with respect to an anchor assembly; and FIG. 4B depicts the lead in cooperation with the lead anchoring structure of the anchor assembly.

FIG. 6 is a schematic view of an anchor assembly that includes a hinged region.

FIG. 7A is a schematic view of an anchor assembly that includes a device anchoring structure; and FIG. 7B is a schematic view of the anchor assembly of FIG. 7A in cooperation with a device having a device anchor.

FIG. 7C is a schematic view of an anchor assembly that includes a device anchoring structure; FIG. 7D is a schematic view and FIG. 7E is a perspective view of a device that includes device anchors configured to cooperate with the device anchoring structures of the anchor assembly of FIG. 7C; and FIG. 7F shows the device in cooperation with the anchor assembly of FIG. 7C.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular frets "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

"Exemplary or representative" is used in the sense of "for example" or "for the purpose of illustration", and not in a limiting sense. Disclosed herein are systems that include at least one anchor assembly and at least one lead. The systems can be utilized for and implanted in a patient for various uses. For purposes of simplifying the present disclosure, the term "patient" is used herein to refer to any environment in which an implantable device is or can be implanted, whether or not the implant or connection is carried out for medical purposes. The patient may also be referred to by the term "body" to refer to the patient's body. In embodiments, the systems can be utilized for stimulation of one or more nerves in a patient. In embodiments, the systems can be utilized for occipital nerve stimulation.

Figure 1A:
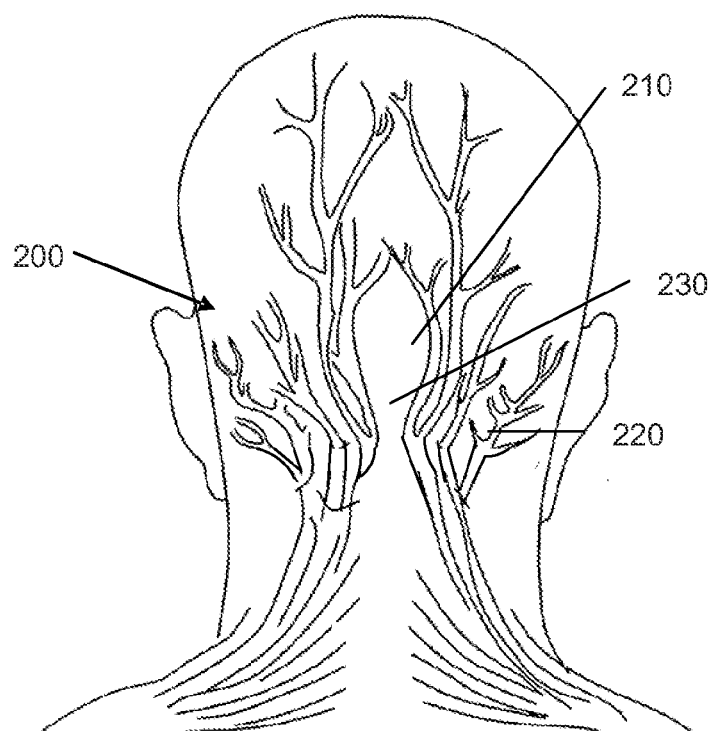
FIG. 1A is a schematic diagram showing the left and right occipital nerves of a subject.

Referring to FIG. 1A, as used herein, "occipital nerve" includes the greater occipital nerve 210, the lesser occipital nerve 220 and the third occipital nerve 230. The greater and lesser occipital nerves are spinal nerves arising between the second and third cervical vertebrae (not shown). The third occipital nerve 230 arises between the third and fourth cervical vertebrae. The portion of the occipital nerve 200 to which an electrical signal is to be applied may vary depending on the disease to be treated and associated symptoms or the stimulation parameters to be applied.

Various types of leads can be utilized to provide stimulation to various portions of the occipital nerve. In embodiments, the leads 800 and 800' include distal portions 874, 874' that contain electrodes that are placed to allow bilateral application of electrical signals to the occipital nerve 200 at a level of about C1 to about C2 or at a level in proximity to the base of the skull. The position of the electrode(s) may vary. It will be understood that the electrode need not, and in various embodiments does not, contact the nerve to apply the signal to the nerve, it will be further understood that a signal may be applied to any suitable portion of an occipital nerve, whether at a trunk, branch, or the like. In various embodiments, one or more electrodes are placed between about 1 cm and about 8 cm from the midline to effectively provide an electrical signal to the occipital nerve 200.

Figure 1B:
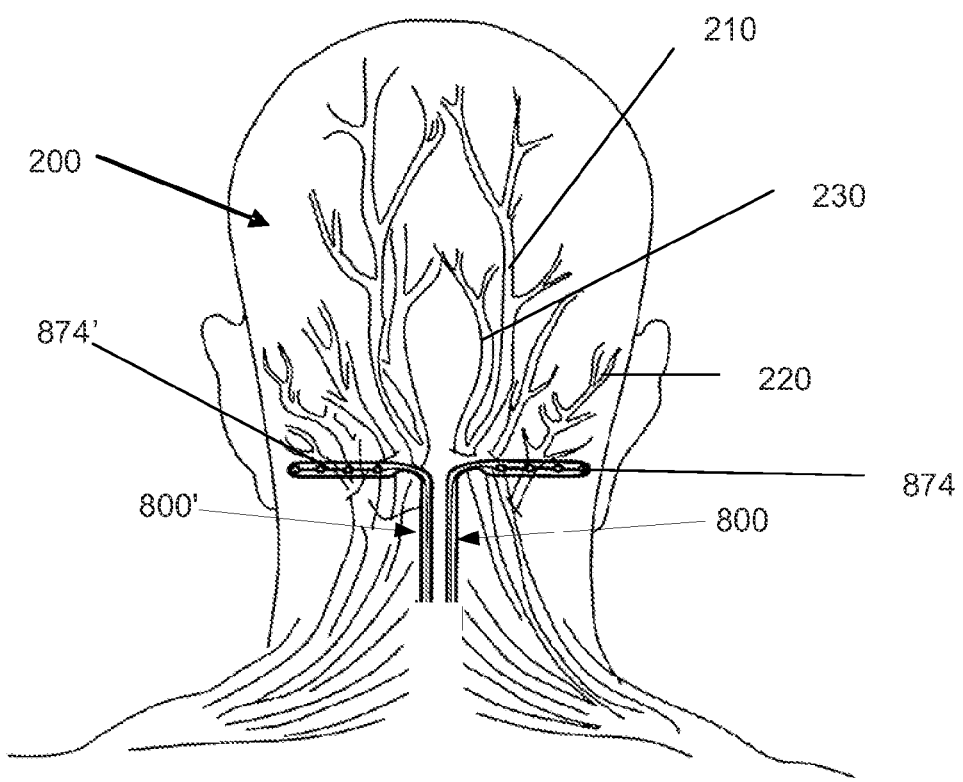
FIG. 1B is a schematic diagram showing leads implanted in a subject and positioned to apply an electrical signal to left and right occipital nerves.

As shown in FIG. 1B, the leads 800, 800' may include paddle shaped distal portions 874, 874' containing electrodes. Such paddle shaped leads are often referred to as surgical leads. Examples of surgical leads that may be modified to form leads as described herein include Medtronic Inc.'s Resume, SymMix, On-Point, or Specify series of leads. Surgical leads typically contain electrodes that are exposed through one face of the paddle, providing directional stimulation. As shown in FIG. 6B, the leads may include distal portions 874, 874' that include electrodes that are generally cylindrically shaped. Such leads are often referred to percutaneous leads. Examples of percutaneous leads that may be modified to form leads as described herein include Medtronic Inc.'s Quad Plus, Pisces Quad, Pisces Quad Compact, or 1×8 SubCompact, 1×8 Compact, and 1×8 Standard leads. Such percutaneous leads typically contain ring electrodes that apply an electrical stimulation signal to tissue in all directions around the ring. Accordingly, the amplitude of the signal (and thus the energy required from the signal generator) applied may be greater with percutaneous leads that surgical leads for occipital nerve therapies.

An exemplary system, as disclosed herein is illustrated in FIG. 2A. An exemplary system 100 in FIG. 2A can include an anchor assembly 110 and at least one lead 120. Systems can also include more than one such anchor assembly, more than one such lead, or more than one such anchor assembly and more than one such lead. Embodiments include one anchor assembly and at least two leads. Embodiments include one anchor assembly and two leads.

The anchor assembly 110 illustrated in FIG. 2A includes a based plate 105. The base plate 105 is generally the body of the anchor assembly. The anchor assembly 110 also includes at least one anchoring structure 140. The particular embodiment depicted in FIG. 2A includes two anchoring structures 140a and 140b. Although the anchoring structures 140a and 140b are depicted as oval or circular in nature, it is to be understood that any geometrical configuration can be utilized. The at least one anchoring structure is configured to be anchored to or in a patient. In embodiments, the anchor assembly is configured to be implanted in a patient and the anchoring structure is configured to allow the anchor assembly to be reversibly or irreversibly anchored to part of the patient's anatomy. In embodiments, the system is configured to be implanted in a patient's head. In embodiments, a disclosed system can be utilized to provide occipital nerve stimulation.

Various embodiments of anchor assemblies can include various numbers of anchoring structures. Various embodiments of anchor assemblies disclosed herein can include a plurality of anchoring structures. The anchor assembly an be configured with anchoring structures at various different locations on the anchor assembly. For example, anchoring structures (shown as undashed oval structures) can be placed around the entire periphery of the anchor assembly 111 as seen in FIG. 2B, around only a portion of the periphery of the anchor assembly 112 as seen in FIG. 2C, or distributed across the entire anchor assembly 113 as seen in FIG. 2D. The use of anchor assemblies with anchoring structures placed at numerous for example greater than two, greater than three, etc.) different locations can afford more flexibility in securing the anchor assembly to the patient. In embodiments where numerous anchoring structures are included at various different locations on an anchor assembly, not all of the anchoring structures need be utilized when securing the anchor assembly in a patient.

In embodiments, the at least one anchoring structure can include a hole (or a pass through, or a void) that allows the anchor assembly to be sutured in place. For example, suture material can be placed through the hole and secured to some portion of the patient's anatomy. In such a case, the suture in combination with the anchoring structure can function to maintain the anchor assembly in or at a location in a patient. In embodiments, the at least one anchoring structure can include a portion that can receive a different type of securing structure. For example, the at least one anchoring structure can include a portion (for example threads) that can receive a screw shaped securing structure. In embodiments, the at least one anchoring structure can include a portion that can be secured to a portion of the patient's anatomy with a surgical adhesive. Embodiments such as those depicted in FIG. 2D, with anchoring structures in the interior portions of the anchor assembly, as opposed to the periphery, can be advantageously utilized with securing methods other than suturing.

It will be understood by one of skill in the art, having read this specification, that various different combinations of types of anchoring structures, sizes of anchoring structures, locations of anchoring structures, and numbers of anchoring structures can be utilized in anchor assemblies as disclosed herein. In embodiments, an anchor assembly having anchoring structures that are secured using sutures can be located on the periphery of the anchor assembly and anchoring structures that are secured using some other method (for example surgical adhesive or surgical screws for example) can be located on the interior portions of the anchor assembly.

Referring again to FIG. 2A, an anchor assembly 110 also includes at least one lead anchoring structure 150. Although the lead anchoring structure 150 is depicted as rectangular, it is to be understood that any geometrical configuration can be utilized. The particular embodiment depicted in FIG. 2A includes four lead anchoring structures 150a, 150b, 150c, and 150d. The at least one lead anchoring structure is configured to secure at least one lead to the anchor assembly. In embodiments, the anchor assembly is configured to be implanted in a patient, anchored in the patient via the at least one anchoring structure, and the at least one lead anchoring structure is configured to allow leads to be reversibly or irreversibly anchored to the anchor assembly.

Various embodiments of anchor assemblies can include various numbers of lead anchoring structures. Various embodiments of anchor assemblies disclosed herein can include a plurality of lead, anchoring structures. The anchor assembly can be configured with lead anchoring structures at various different locations on the anchor assembly. For example, lead anchoring structures (shown as dashed rectangular structures) can be placed around the entire periphery of the anchor assembly 114 as seen in FIG. 2E, around only a portion of the periphery of the anchor assembly 115 as seen in FIG. 2F, or distributed across the entire anchor assembly 116 as seen in FIG. 2G. The use of anchor assemblies with lead anchoring structures placed at numerous (for example greater than two, greater than three, etc) different locations can afford more flexibility in securing the lead (or leads) to the anchor assembly. In embodiments where numerous lead anchoring structures are included at various different locations on an anchor assembly, not all of the lead anchoring structures need be utilized when securing the lead (or leads) to the anchor assembly.

It will be understood by one of skill in the art, having read this specification, that various different combinations of types of lead anchoring structures, sizes of lead anchoring structures, numbers of lead anchoring structures, and locations of lead anchoring structures can be utilized in anchor assemblies as disclosed herein. It will also be understood by one of skill in the art, having read this specification, that various different combinations of types of anchoring structures and lead anchoring structures, sizes of anchoring structures and lead anchoring structures, numbers of anchoring structures and lead anchoring structures, and locations of anchoring structures and lead anchoring structures can be utilized in anchor assemblies as disclosed herein.

Lead anchoring structures generally function by cooperating with a lead or a portion of a lead to secure the lead to the anchor assembly. A lead which is to be utilized with a disclosed anchor assembly generally includes one or more lead anchors. A lead anchor is a structure that is built into a lead or can be added to a lead that cooperates with a lead anchoring structure on an anchor assembly to reversibly or irreversibly secure the lead to the anchor assembly. FIG. 2A illustrates a lead 120 that includes a lead body 123 having at least one lead anchor 160. In embodiments, the lead anchor 160 is disposed on (or in) the lead between an electrode region 125 (that can be located generally on or in the distal portion 126 of the lead body 123 and includes one or more electrodes) and the proximal portion 127 of the lead 120. The at least one lead anchor 160 can be an integral part of the lead 120 or the lead body 123 or can be an element that is mechanically attached and/or fastened to the lead body 123. In embodiments, the lead anchors can be attached after fabrication of the lead. Such a lead may allow for easier placement of the lead through a delivery device, which can often have relatively small inner diameters.

Generally, the lead anchor is configured to have a mating relationship with the lead anchoring structure of the anchor assembly. For example, as in one having a male configuration and the other having a female configuration. It should be understood by one of skill in the art, having read this specification, that relationships that are opposite to those discussed herein (for example if a relationship has a protrusion as the lead anchor and an indentation as the lead anchoring structure, the opposite a protrusion as the lead anchoring structure and an indentation as the lead anchor) are also contemplated for both lead anchor-lead anchoring structures and device anchor-device anchoring structures.

FIG. 3A illustrates a schematic view of an exemplary lead anchor 360 on the lead body 305 of a lead 300. FIG. 3B illustrates a schematic perspective view of the exemplary lead 300 in relation to a portion of an anchor assembly 310 that it can be utilized with. The anchor assembly 310 includes a lead anchoring structure 350 that is configured to have a mating relationship with the lead anchor 360 of the lead 300. In this particular embodiment, the two have spherical based configurations. FIG. 3C illustrates the lead 300 and the anchor assembly 310 once the two are contacted with and secured to each other. In embodiments, the lead anchor 360 can stay engaged with the lead anchoring structure 350 (and/or vice versa) to secure the lead 300 to the anchor assembly 310 based entirely on the configuration of the two structures. In other embodiments, the lead anchor 360 can stay engaged with the lead anchoring structure 350 (and/or vice versa) to secure the lead 300 to the anchor assembly 310 based on the configuration of the two structures and other factors (for example, addition of adhesive or the material making up the two structures).

FIG. 4A illustrates a schematic view of an exemplary lead anchor 460 on the lead body 405 of a lead 400. FIG. 4B illustrates a schematic perspective view of the exemplary lead 400 in relation to a portion of an anchor assembly 410 that it can be utilized with. FIGS. 4A and 4B, numbered similarly to FIGS. 3A and 3B, can function in the same fashion as that of FIGS. 3A and 3B, but the lead anchoring structure 450 and the lead anchor 460 have pyramidal type structures. Other types of geometrically shaped configurations having mating relationships other than those exemplified herein can also be utilized for the lead anchor and lead anchoring structure.

Figure 5A:
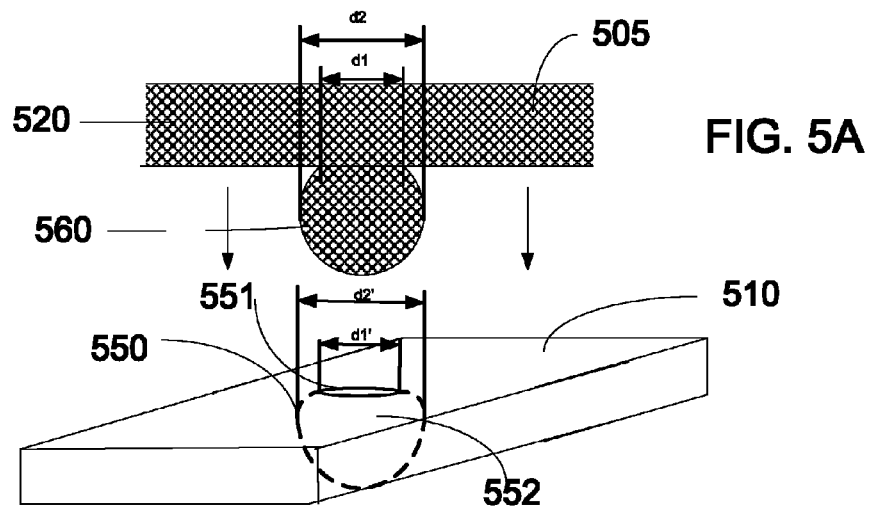
FIG. 5A is a schematic perspective view of a lead having a compression fit configuration with respect to an anchor assembly.

FIG. 5A illustrates another type of embodiment. The embodiment depicted in FIG. 5A has a compression fit mating relationship between the lead anchor 560 positioned on the lead body 505 and the lead anchoring structure 550. Although the embodiment depicted in FIG. 5A has a spherical geometry, it should be understood by one of skill in the art having read this specification, that geometries other than spherical could also be utilized with compression fit mating relationships. As seen in FIG. 5A, the lead anchor 560 has a maximum diameter d2 and a minimum diameter d1. The anchor assembly 510 includes at least one lead anchoring structure 550 that has an opening 551 with a diameter d1' that is substantially equivalent to the minimum diameter d1 of the lead anchor 560; and a cavity 552 with a maximum diameter d2' that is substantially equivalent to the maximum diameter d2 of the lead anchor 560. With such a configuration, the lead anchor 560 can be fit into the lead anchoring structure 550 via application of some level of force.

Figure 5B:
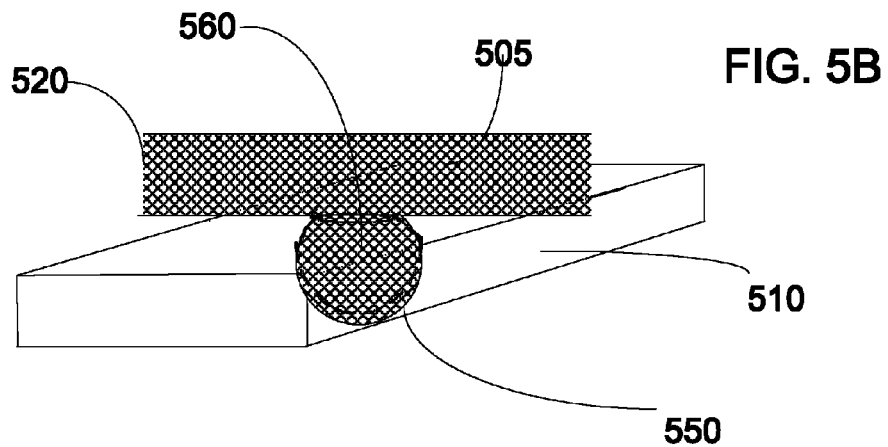
FIG. 5B depicts the lead in cooperation with the lead anchoring structure of the anchor assembly.

As seen in FIG. 5B, once the lead anchor 560 is in the cavity 552 of the lead anchoring structure 550, at least some level of pulling force is required to remove the lead anchor 560 from the lead anchoring structure 550. This is the case because the maximum diameter of the lead anchor 560 is greater than the diameter d1' of the opening 551. With such a mating relationship, the lead anchor 560 and lead anchoring structure 550 can generally function, without additional assistance, in securing the lead 520 to the anchor assembly 510. In such embodiments, the anchor assembly, or at least the area immediately surrounding the lead anchoring structure can be made of a material that has at least some level of elasticity to allow the area around the opening 551 to reversibly expand to allow the lead anchor 560 to be fit into the lead anchoring structure 550.

Figure 5C:
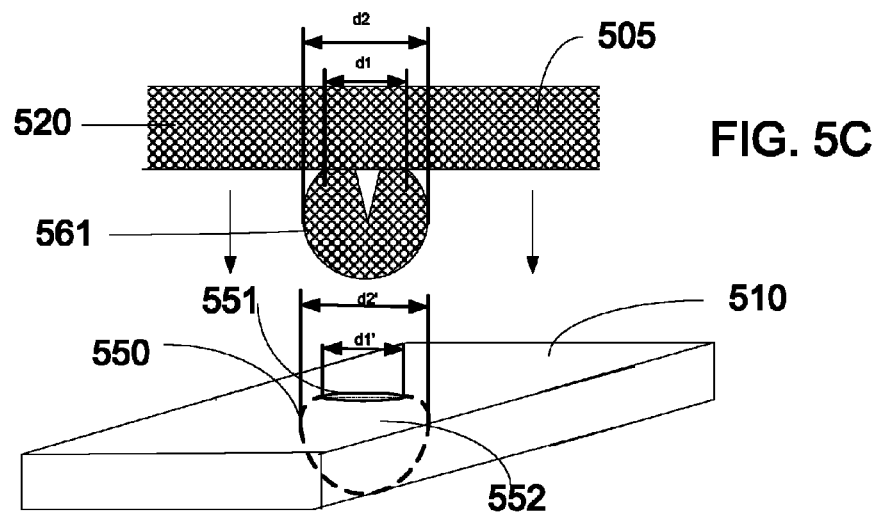
FIG. 5C is a schematic perspective view of a lead having another embodiment of a mating relationship with the lead anchoring structure.
Figure 5D:
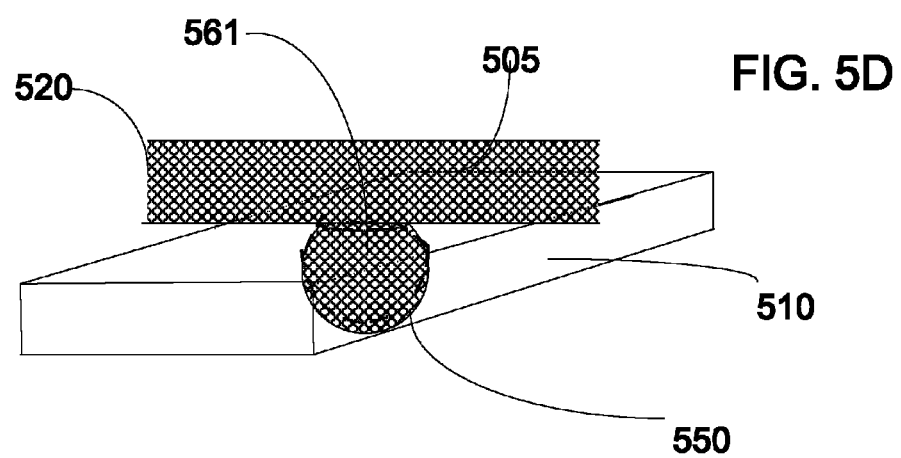
FIG. 5D depicts the lead in cooperation with the lead anchoring structure of the anchor assembly in FIG. 5C.

FIGS. 5C and 5D illustrate another example of a lead anchor 561 and a lead anchoring structure 550. Such an embodiment can be referred to as having a compressible lead anchor. The lead anchor 561 depicted herein is similar to that depicted in FIGS. 5A and 5B, except that a portion of the interior of the material making up the lead anchor 561 is not present. This can allow the remaining material of the lead anchor 561 to collapse inward allowing it to fit through the opening 551 of the lead anchoring structure 550. The ability of the lead anchor 561 to collapse inward on itself can be utilized with any type of geometrical configuration of a lead anchor 561. Such configurations can also be combined with having at least the material surrounding the opening 551 of the lead anchoring structure 550 be somewhat elastic.

Figure 5E:
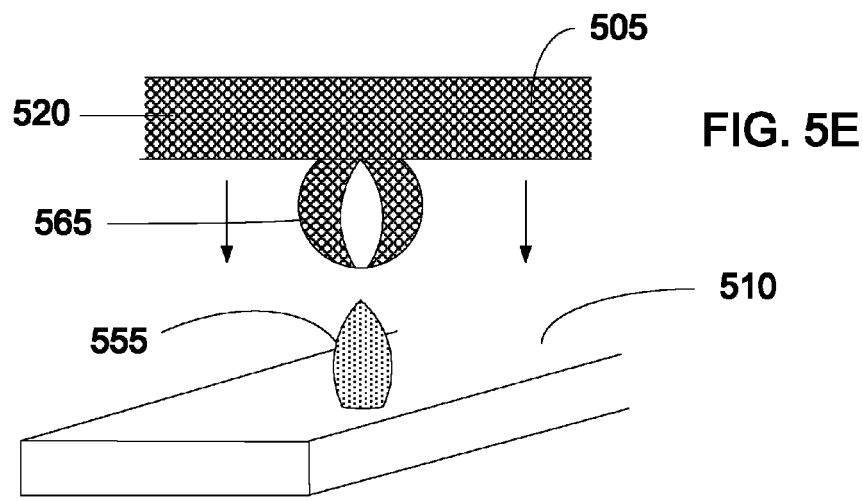
FIG. 5E is a schematic perspective view of a lead having a clam shell like configuration with respect to the anchor assembly.
Figure 5F:
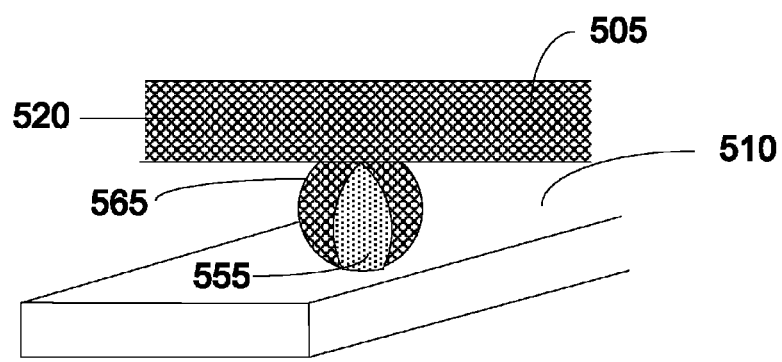
FIG. 5F depicts the lead in cooperation with the lead anchoring structure of the anchor assembly.

Other types of mating relationships not specifically depicted in the figures can also be present between the lead anchor and the lead anchoring structure can also be utilized. For example, the lead can include multiple protrusions that are meant to be accepted by an indentation or void in the anchor assembly. Alternatively, the lead anchor and lead anchoring structure could function in an analogous fashion to a snap system. In such a snap system, the lead anchor could have a protrusion and the lead anchoring structure could have an indentation that accepts the protrusion (or vice versa). Alternatively, the lead anchor and lead anchoring structure could function by actuating one or more portions of the lead anchor (and/or lead anchoring structure) to mechanically grasp some portion of the lead anchoring structure (or vice versa). Such a configuration could be referred to as a clam shell type connection. An exemplary embodiment of an anchor assembly and lead that could be referred to as having a clam shell type mating relationship can be seen in FIGS. 5E and 5F. As seen there, the lead 520 includes a lead anchor 565 that can be actuated by force or a mechanical system (not shown), by application of the lead anchor 565 to the lead anchoring structure 555 on the anchor assembly 510, or some combination thereof. As seen in FIG. 5F, once the lead anchor 565 contacts the lead anchoring structure 555, the bias of the lead anchor 565 engages the lead anchoring structures 555 to maintain the lead anchor 565 on the lead anchoring structure 555.

Exemplary anchor assemblies can include a base plate (or anchor assembly body) and various components that can either be added to the base plate (or anchor assembly body) or can be formed integrally in the anchor assembly body. Exemplary anchor assemblies may be made of a biocompatible metal such as titanium. When referring to materials that can be utilized to make anchor assemblies, it should be understood by one of skill in the art, having read this specification, that the materials listed may be referring to the entire anchor assembly including all of the components, the body of the anchor assembly without any of the components, or a portion of the components as well as the body of the anchor assembly. Generally, any combinations of materials can be utilized for portions of the components or some number of the components and/or anchor assembly body. In further embodiments anchor assemblies may be made of a polymer, such as, for example, polyurethane, polycarbonate, polyether ether ketone (PEEK). Other suitable materials may include material that is used in making suture materials, such as polypropylene, polyester, or nylon. Other materials may add various properties as desired, such as being elastic. Elastic materials may include copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes and the like. Any methods of constructing anchor assemblies, and anchors (e.g. lead anchors or device anchors for example) known to one of skill in the art, having read this specification, can be utilized to manufacture anchor assemblies, leads, and devices disclosed herein.

Anchor assembly bodies may have different configurations. In embodiments, the anchor assembly body can be non-planar. For example, the anchor assembly body can be shaped to mirror the shape of the skull. In other embodiments, the anchor assembly body can more readily follow the shape of the skull by being substantially planar when not implanted, but be made of a material that once attached to the skull, via the anchoring structures, it at least somewhat conforms to the shape of the skull surface. In yet other embodiments, the anchor assembly body can include a hinged region. An example of such an embodiment is depicted in FIG. 6. The anchor assembly 610 depicted in FIG. 6 includes an anchor assembly body 605, at least one (in this case two) anchoring structures 640, at least one (in this case four) lead anchoring structures 650, and a hinge 670 that attaches to a hinged region 675 of the anchor assembly body 605. The hinge 670 functions to allow the anchor assembly body 605 to bend at the hinged region 675 in order to more closely follow the shape of the skull (or other body portion into which it is implanted).

In embodiments anchor assemblies can also include one or more device anchoring structures. A device anchoring structure functions to anchor a device, such as an implantable medical device. In embodiments, the implantable medical device can be an implantable neurostimulator. In such embodiments, the device anchoring structure can be referred to as a stimulator anchoring structure. A stimulator anchoring structure can function to secure a neurostimulator (or other implantable medical device) to the anchor assembly, and once the anchor assembly is anchored to the patient, the neurostimulator is also anchored to the patient.

FIG. 7A illustrates an anchor assembly 700 that includes a base plate 705 having at least one (in this example two) anchoring structures 740, at least one (in this example 12, of which three are particularly noted) lead anchoring structure 750, and a stimulator anchoring structure 780. The stimulator anchoring structure can be located at any point on the base plate 705, and can generally be any structure or structures that can function in cooperation with the neurostimulator (for example) to reversibly or irreversibly secure the neurostimulator to the anchor assembly.

The example depicted in FIG. 7A shows the stimulator anchoring structure 780 as including two notches 781. In such an embodiment, a neurostimulator would be configured to have one or more structures that cooperate with the two notches to secure the neurostimulator to the anchor assembly. FIG. 7B illustrates the anchor assembly 700 of FIG. 7A secured to a neurostimulator 790. As seen in FIG. 7B, the neurostimulator 790 in this example can include notches which have a mating relationship with the notches included in the stimulator anchoring structure 780.

In other embodiments (not specifically illustrated in the figures), the stimulator anchoring structure can include a cavity that a properly configured neurostimulator can fit into, thereby securing the neurostimulator to the anchor assembly. Other relationships between the neurostimulator and the anchor assembly can also function to secure the neurostimulator to the anchor assembly. In embodiments, neurostimulators configured to be secured to an anchor assembly via the stimulator anchoring structure can be microstimulators. Generally, a microstimulator is a stimulator that has a smaller volume (in some embodiments a significantly smaller volume) than a standard neurostimulator.

FIG. 7C illustrates an embodiment of an anchor assembly 700 that also includes a device anchoring structure or more specifically a stimulator anchoring structure 780. The stimulator anchoring structure 780 in this example includes at least one pin, and in this case, two pins 784. The stimulator anchoring structure 780 can either be recessed in the anchor assembly 700, in which case the pins can be protrusions in the recession; or be generally planar with the plane of the anchor assembly, in which case the pins can be protrusions on the plane of the anchor assembly. FIGS. 7D and 7E depict an exemplary device or stimulator 790 that can be utilized with the anchor assembly 700 including the stimulator anchoring structure 780 as exemplified above. The stimulator 790 in this embodiment includes at least one, and in this case two stimulator anchors 791 (in this case indentations) that are configured to accept and mate with the pins 784 of the stimulator anchoring structure 780 of the anchor assembly. FIG. 7F shows a cross section of a portion of an anchor assembly 700 with the stimulator 790 depicted in FIGS. 7D and 7E placed therein. As seen there, the stimulator 790 fits within the recess that forms part of the stimulator anchoring structure 780 and the indentations 791 fit and mate with the pins 784. It should be understood by one of skill in the art that any of the mating relationships discussed above (e.g. compression fits, clam shell, compressible anchors), other methods discussed above (screws or adhesives for example), or any other known to one of skill in the art, having read this specification can be utilized to maintain the stimulator 790 with stimulator anchors 791 within the stimulator anchoring structure 780.

Figure 8A:
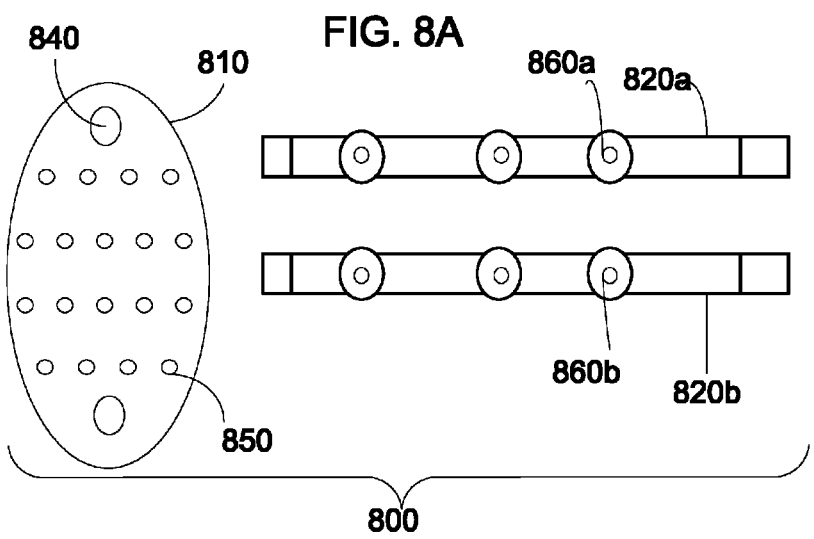
FIG. 8A is a schematic view of a system that includes an anchor assembly and two leads.

Systems as disclosed herein can also optionally include other components. An embodiment of a disclosed system 800 is illustrated in FIG. 8A. This exemplary system 800 includes an anchor assembly 810, a first lead 820a, and a second lead 820b. The anchor assembly 810 can include features such as those discussed above. For example, the particular embodiment included in FIG. 8A includes 18 lead anchoring structures (one of which is designated as lead anchoring structure 850) and two anchoring structures (one of which is designated as anchoring structure 840). The leads 820a and 820b in the exemplified system each includes three lead anchors (one of which is each designated as 860a and 860b). Systems as disclosed herein can also optionally include other components.

Such a system could also include an implantable medical device that is not configured to be anchored to the anchor assembly. Nearly any implantable medical device or system employing leads may be used in conjunction with the anchor assembly described herein. Representative examples of such implantable medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like. For purposes of occipital nerve stimulation, electrical signal generators such as Medtronic, Inc.'s Restore® or Synergy® series of implantable neurostimulators may be employed. Other components not illustrated or discussed herein (such as lead extensions) can also be optionally included in such a system.

Figure 8B:
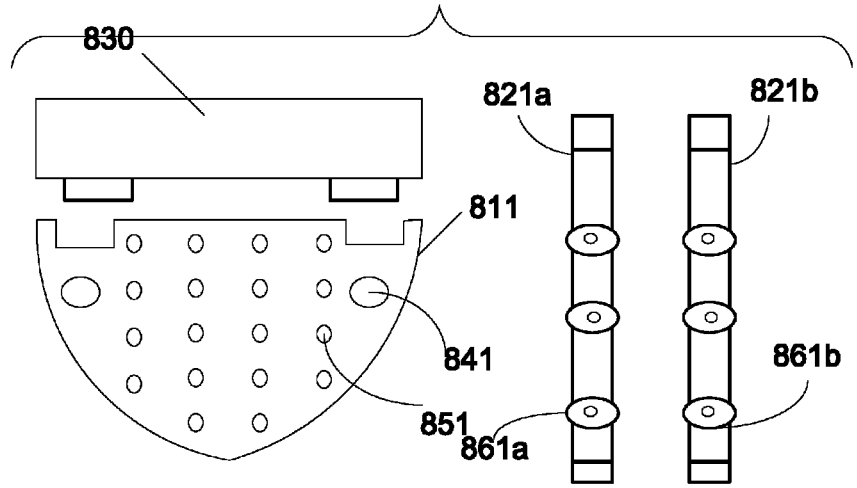
FIG. 8B is a schematic view of a system that includes an anchor assembly, an implantable medical device, and two leads.

Another embodiment of a disclosed system 801 is illustrated in FIG. 8B. This exemplary system 801 includes an anchor assembly 811, a first lead 821a, a second lead 821b, and an implantable medical device 830. As seen in this embodiment, the implantable medical device 830 is configured to be secured to the anchor assembly 811 via stimulator anchors present on the implantable medical device. For example, the particular embodiment included in FIG. 8B includes 18 lead anchoring structures (one of which is designated as lead anchoring structure 851) and two anchoring structures (one of which is designated as anchoring structure 841). Other components not illustrated or discussed herein can also be optionally included in systems disclosed herein.

Figure 8C:
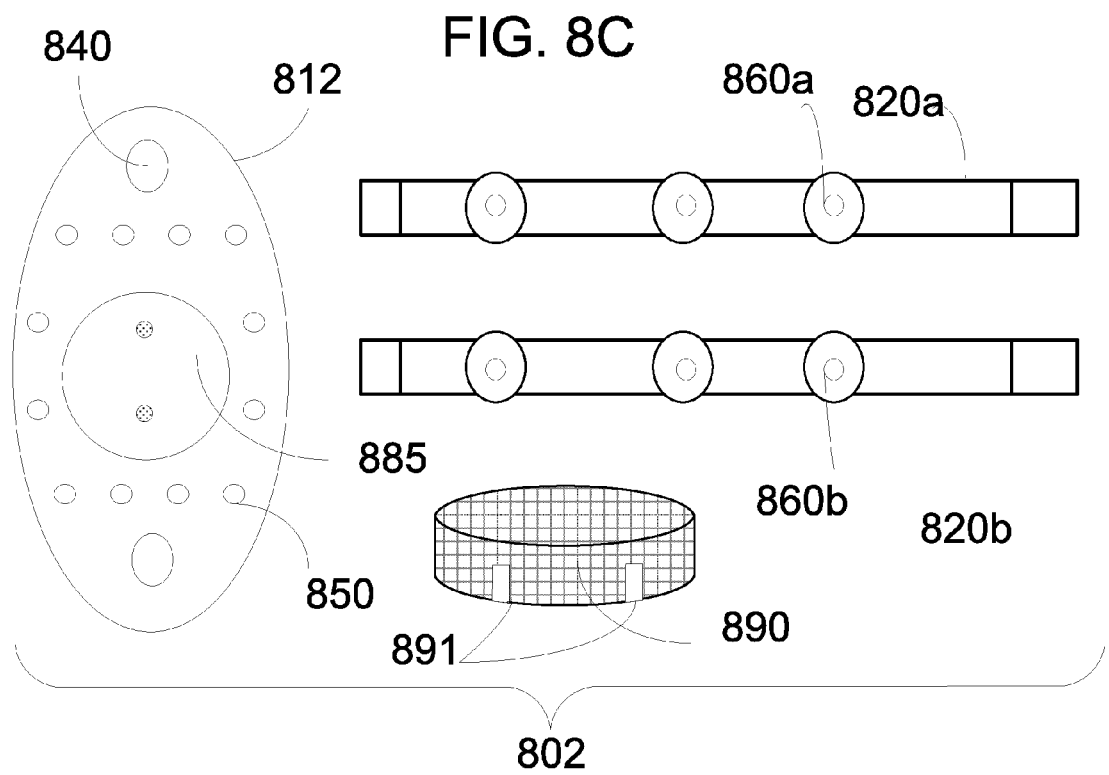
FIG. 8C is a schematic view of a system that includes an anchor assembly, an implantable medical device, and two leads.

FIG. 8C illustrates another embodiment of a system 802. This exemplary system 802 includes an anchor assembly 812, a first lead 821a, a second lead 821b, and an implantable medical device 890. As seen in this embodiment, the implantable medical device 890 is configured to be secured to the anchor assembly 812 via stimulator anchors 891 present on the implantable medical device 890 and device anchoring structure 885 on the anchor assembly 812.

It should be understood that any combination of features can be included in an anchor assembly and/or system as disclosed herein, even if such features were not specifically discussed in combination herein.

Methods of anchoring at least one lead in a patient are also disclosed herein. In embodiments, such a method can be utilized to anchor at least one lead in a head of a patient. Such methods can include the steps of anchoring an anchor assembly, as discussed above in the head of a patient, and securing at least one lead as discussed above to the anchor assembly, wherein the at least one lead anchor of the lead and the lead anchoring structure are configured to cooperate to secure the at least one lead to the anchor assembly, thereby anchoring the at least one lead in the head of the patient. In embodiments, the anchor assembly can be anchored in the head of the patient before the lead is secured to the anchor assembly. In embodiments, the anchor assembly can be anchored in the head of the patient after, or at substantially the same time (for example by another doctor) the lead is secured to the anchor assembly.

The particular reason for implanting the system in the patient can dictate, at least in part, the particular location of implantation. The particular details of the anchor assembly, and more specifically the anchoring structure (or anchoring structures) can dictate at least in part, how the step of anchoring the anchor assembly in the patient is carried out. In embodiments, the anchor assembly can be anchored in the head of the patient by suturing the anchoring structure in the head of the patient. In embodiments more than one method of anchoring the anchor assembly in the patient can be utilized to anchor the anchor assembly in a single patient. In embodiments all of the anchoring structures in an anchor assembly can be utilized, and in embodiments, less than all of the anchoring structures in an anchor assembly can be utilized.

The particular process of securing the at least one lead to the anchor assembly can depend at least in part on the type of mating configuration between the lead anchoring structure and the lead anchor. For example, in embodiments where the two have a compression fit relationship, force can be applied to the lead anchor to ease it into the lead anchoring structure. Other types of mating relationships can utilize different methods of securing the lead to the anchor assembly. In embodiments, a lead anchor can be secured to an anchor assembly utilizing a first lead anchoring structure on the anchor assembly, can be removed and then a different lead anchoring structure on the anchor assembly can be utilized. Methods as disclosed herein can also further include securing at least a second lead to the anchor assembly.

In embodiments a method as disclosed herein can include determining the desired placement of at least a first lead within a patient, attaching an anchor assembly to a patient, and attaching the lead anchor of the first lead to the attached anchor assembly. In embodiments, the anchor assembly can be attached to the patient before the desired placement of the first lead is determined; and in embodiments it can be done after. Embodiments of methods can also include determining the desired placement of a second lead within a patient and attaching the lead anchor of the second lead to the attached anchor assembly. In embodiments, a device including a device anchor can be attached to a device anchoring structure of the anchor assembly; this can be done before or after the desired placement of a first and/or second lead is determined, before or after the first and/or second lead is attached to the anchor assembly, or some combination thereof. In embodiments, the device can be secured to the anchor assembly before the anchor assembly is implanted in the patient. This can decrease the number of steps and/or decrease the number of individual components that must be placed into a patient. In such embodiments, the anchor assembly can function as a "third hand" to maintain desired locations of leads once they have been determined. This can assist such surgical procedures because it allows a lead to be easily kept in place once a desired location has been found for the electrodes contained thereon (for example via test stimulation), without allowing movement of the electrodes while other portions of the procedure are carried out.

Methods disclosed herein can also include the step of securing a stimulator to the anchor assembly. This step can be carried out when an anchor assembly that includes stimulator anchoring structure(s) is utilized. The particular process of securing the stimulator to the anchor assembly can depend at least in part on the type of mating configuration between the stimulator anchor and the stimulator anchoring structure.

Figure 9:
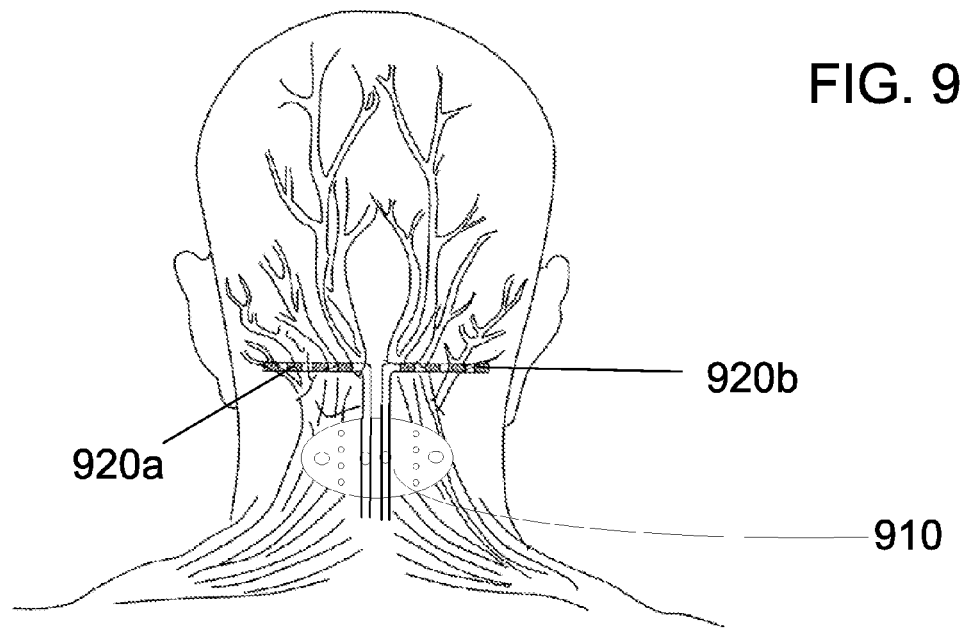
FIG. 9 is a schematic view of an anchor assembly and two leads being implanted in a subject for occipital nerve stimulation.

FIG. 9 shows the head of a patient with two leads 920a and 920b implanted therein. The two leads 920a and 920b are secured to the anchor assembly 910, which is anchored to some portion of the anatomy of the patient. In embodiments, an anchor assembly can be attached to subcutaneous tissue within the head of a patient. In embodiments, an anchor assembly can be attached to fascia within the head of a patient.

Various embodiments of systems and methods have been described above with regard to occipital nerve stimulation. However, it will be understood that such leads, devices, systems, and methods may be used for any other therapeutic or monitoring purpose.

Thus, embodiments of ANCHOR ASSEMBLY FOR USE IN OCCIPITAL NERVE STIMULATION are disclosed. One skilled in the art will appreciate that the leads, extensions, connectors, devices such as signal generators, systems and methods described herein can be practiced with embodiments other than those disclosed. The disclosed embodiments are presented for purposes of illustration and not limitation.

What is claimed is:

1. A system comprising:
   a. an anchor assembly, the anchor assembly comprising:
      i. a base plate;
      ii. at least one anchoring structure formed in or on the base plate, the anchoring structure configured to be anchored in a head of a patient; and
      iii. at least one lead anchoring structure formed in or on the base plate; and
   b. at least one lead, the at least one lead comprising:
      i. a lead body extending from a distal end to a proximal end;
      ii. at least one electrode located on or in the distal end of the lead body; and
      iii. at least one lead anchor located on or in the lead body proximal to the electrode, wherein the lead anchor has a spherical geometry with a maximum diameter $d2$ and a minimum diameter $d1$, the lead anchoring structure comprises an opening with a diameter $d1'$ and a cavity with a maximum diameter $d2'$, and $d1$ and $d1'$ are substantially equivalent and $d2$ and $d2'$ are substantially equivalent, and
   wherein the at least one lead anchor of the lead and the lead anchoring structure are configured to have a compression fit mating relationship between the lead anchor and the lead anchoring structure to secure the at least one lead to the anchor assembly.

2. The system according to claim 1 further comprising at least two anchoring structures.

3. The system according to claim 1 further comprising a plurality of lead anchoring structures.

4. The system according to claim 1, wherein the at least one anchoring structure is configured to be sutured in the head of the patient.

5. The system according to claim 1, wherein the at least one lead comprises a plurality of lead anchors.

6. The system according to claim 1 further comprising at least two leads.

7. The system according to claim 1, wherein at least the area immediately surrounding the lead anchoring structure is made of a material that is at least somewhat elastic.

8. The system according to claim 1, wherein the interior of the material making up the spherical geometry of the lead anchor is not present.

* * * * *